United States Patent [19]

Mizia et al.

[11] Patent Number: 5,210,284

[45] Date of Patent: May 11, 1993

[54] CONTINUOUS PROCESS FOR THE PREPARATION OF ISOCYANATES FROM URETHANES

[75] Inventors: Franco Mizia, Milan; Carlo Calderoni, Forlí, both of Italy

[73] Assignee: Enichem Synthesis S.p.A., Palermo, Italy

[21] Appl. No.: 810,143

[22] Filed: Dec. 19, 1991

[30] Foreign Application Priority Data

Dec. 21, 1990 [IT] Italy ................................ 22475 A/90

[51] Int. Cl.$^5$ .......................................... C07C 263/04
[52] U.S. Cl. .................................... 560/345; 560/355; 560/356; 560/358; 560/360
[58] Field of Search ............... 560/345, 355, 356, 358, 560/360

[56] References Cited

U.S. PATENT DOCUMENTS 4,692,550 9/1987 Engbert et al. ...................... 560/345

Primary Examiner—José G. Dees
Assistant Examiner—Vera C. Clarke
Attorney, Agent, or Firm—Oblon, Spivak, McClelland, Maier & Neustadt

[57] ABSTRACT

Organic mono- or di-isocyanates are prepared by the decomposition of the corresponding urethanes, by means of a continuous process in which:

(a) an urethane flow is continuously fed to a decomposition reactor containing a liquid mixture, composed of a high boiling inert organic solvent, of an unaltered urethane and isocyanate, kept at the boiling conditions of the solvent, at a temperature suitable to decompose the urethane and evaporate the alcohol which is the co-product of the reaction;

(b) the liquid mixture is continuously withdrawn from the reactor in (a) and is fed to a flash equipment, at an operating temperature lower than the decomposition temperature of the urethane, where the isocyanate is partially evaporated and the residuous liquid mixture is recycled to the reactor in (a); and (c) the steam flow generated in (b) is distilled to separate the isocyanate in pure or substantially pure form.

8 Claims, 1 Drawing Sheet

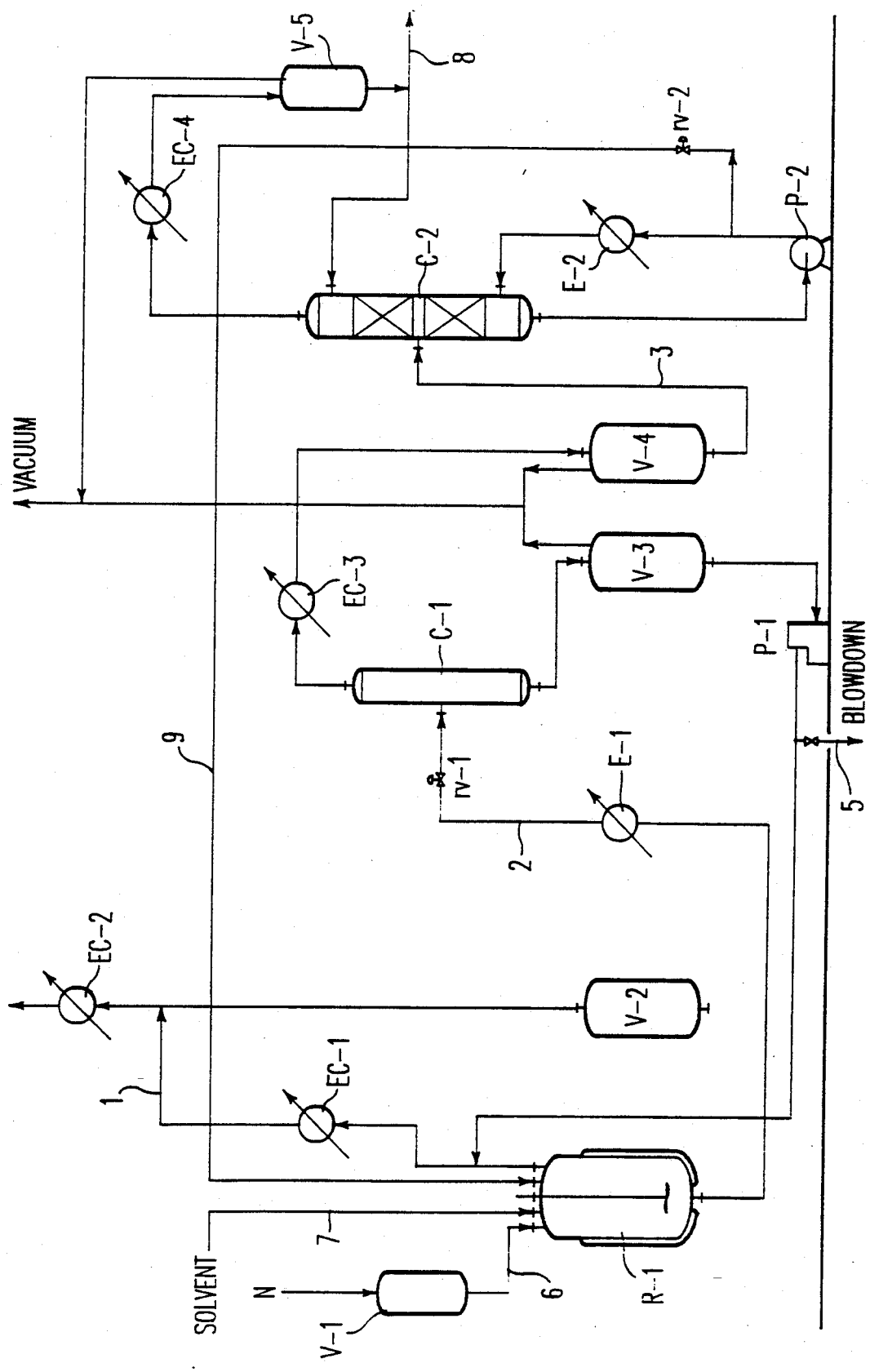

CONTINUOUS PROCESS FOR THE PREPARATION OF ISOCYANATES FROM URETHANES

DESCRIPTION

The present invention concerns a process for the preparation of alkyl or aromatic mono- and di-isocyanates by means of the thermal decomposition of the corresponding urethanes.

Various processes are known for the preparation of isocyanates, based on the decomposition reaction of the urethanes, operating in liquid phase and with a catalyst. In this decomposition an alcohol is formed which is a reaction co-product. In particular, JP 63-211.257 describes a process for the synthesis of isocyanates, by means of the thermal decomposition of the corresponding urethanes, carried out in a high boiling inert solvent, with metal catalysts such as vanadium and chromium. One of the reaction products is withdrawn from the decomposition reactor. Similarly, JP 63-211.256 uses compounds of boron with metals of groups IA and IIA as catalysts. Also in this case one of the reaction products is removed from the decomposition reactor. WO-88.05430 describes a liquid phase process for the synthesis of alkyl di-isocyanates using as catalysts compounds of metals belonging to groups VIA and VIIA, operating at a temperature of 230° C. and at reduced pressure. Both reaction products are removed from the decomposition reactor and recovered by means of two subsequent steps of condensation. Italian Patent Application 20.041 A/89 describes a process for the decomposition of urethanes, carried out without a catalyst, in a boiling solvent. A low boiling solvent, forming an azeotropic mixture with the alcohol, the reaction co-product, is continuously fed to the decomposition reactor kept at 265° C. Both reaction products are continuously removed from the decomposition reactor and recovered in two subsequent condensation steps.

The basic problem in the decomposition of urethanes consists of the tendency of the reaction products, isocyanate and alcohol, to recombine with each other to reform the initial product. This fact, which causes difficulties in separating the reaction products and in recovering them in a sufficiently pure form, has created a considerable drawback in the development of the process on a commercial scale. In catalytic decomposition processes of urethanes, carried out in the liquid phase, there are also problems of purifying the liquid flows from the catalytic residues.

The aim of the present invention is to overcome the above-mentioned drawbacks of the known procedures.

In particular, it has been discovered, according to the present invention, that it is possible to decompose urethanes continuously and selectively, operating in a liquid reaction mixture in which there are constantly limited quantities of unaltered urethane and isocyanate, with the simultaneous elimination of the alcohol, the reaction co-product. It has also been found that it is possible to recover the isocyanate, continuously and in a substantially pure form, by means of the partial evaporation of the liquid mixture, thus preventing the recombination of the reaction products.

On this basis, the aim of the present invention is a simple and practical continuous process which can be easily scaled up to a commercial production, producing isocyanates from the corresponding urethanes with high yields and selectivity.

More specifically, the present invention concerns a continuous process for the production of a mono- or di-isocyanate from the corresponding urethane, according to the following reaction:

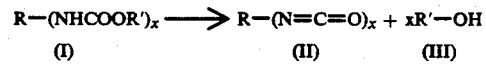

$$R-(NHCOOR')_x \longrightarrow R-(N=C=O)_x + xR'-OH$$
$$(I) \qquad\qquad (II) \qquad\qquad (III)$$

where
R represents a C3–C18 alkyl radical, with a linear or branched chain, possibly having one or more ethylenic unsaturations; a C5–C7 cycloalkyl radical; a monocyclic or polycyclic aryl radical, with condensated or not condensated rings; or a C1–C4 aryl alkyl radical; these radicals may possibly have one or more substituents chosen from the C1–C4 alkyl, C1–C4 alkoxy, nitro, chloro, fluoro or bromo groups;
R' represents a C1–C20 alkyl group; and
x is 1 or 2;
the above process being characterized by the fact that:
(a) a urethane flow (I) is continuously fed to a decomposition reactor containing a liquid mixture, having a substantially constant volume and composition and without any catalytic substances for the decomposition reaction, comprising a high boiling inert organic solvent, containing unaltered urethane (I) with a concentration of from 0.05 to 1.0 equivalent urethane functions and isocyanate (II) having a concentration of from 0.02 to 0.9 equivalent isocyanate functions for every kg of the liquid mixture. The above reactor is kept at the boiling temperature of the solvent and at the decomposition temperature of the urethane (I) in isocyanate (II) and alcohol (III), the decomposition rate of the urethane (I) being comparable to its feeding rate to the reactor, the alcohol (III) being evaporated at a rate substantially equal to that of its formation;
(b) the liquid mixture is continuously removed from the reactor in (a) at a rate which does not substantially vary the volume of the mixture in (a) and is fed to a flash equipment maintained at a temperature lower than the decomposition temperature of the urethane (I). The isocyanate (II) is partially evaporated in the above equipment at a rate which is comparable to that at which it is formed in the reactor in (a), and the residue liquid mixture of the flash is recycled to the reactor in (a); and
(c) the steam flow generated in (b) is continuously removed, condensed and distilled, in a distillation column, to separate the isocyanate (II), in a pure or substantially pure form, as a product of the head of the column. In the preferred form of application, R in the previous formulae represents: an aryl radical deriving from an aromatic monoamine, in particular aniline, and ortho-, meta- or para-substituted anilines with alkyl groups such as methyl, ethyl, propyl, isopropyl and butyl or with groups containing halogens and in particular fluorine, chlorine and bromine; an alkyl radical deriving from an aliphatic monoamine, in particular n-, sec-, and ter-butyl amine, isobutyl amine, 2- and 3-methyl butyl amine, neopentyl amine, n-pentyl amine, n-hexyl amine, cyclohexyl amine, n-octyl amine, n-decyl amine; an alkyl radical deriving from an aliphatic diamine, in particular ethylene diamine, 1,3-propylene diamine, 1,4-butylene diamine, 1,5-pentylene diamine, 1,6-hexamethylene diamine, 3-aminomethyl-3,5,5-trimethylcyclohexyl amine; and R' represents the methyl group.

Examples of urethane (I) which can undergo the decomposition treatment of the present invention are: methyl N-phenyl urethane, methyl N-p-methoxyphenyl urethane, methyl N-p-chlorophenyl urethane, methyl N-m-(trifluoro methyl) phenyl urethane, methyl N-cyclohexyl urethane, methyl N-butyl urethane, 3-methoxy carbonylamino-3,5,5-tri-methyl methoxycarbonylamino cyclohexyl urethane, 1,6-dimethyl hexamethylene urethane. Consequently examples of isocyanate (II) are: phenyl isocyanate, p-methoxyphenyl isocyanate, p-chlorophenyl isocyanate, 3,5-dichlorophenyl isocyanate, isopropyl isocyanate, cyclohexyl isocyanate, butyl isocyanate, m-(trifluoromethyl) isocyanate, isophorone diisocyanate and hexamethylene diisocyanate.

The high boiling inert organic solvent, used in stage (a) of the process, is an organic solvent whose boiling point is at least 40°-50° C. higher than that of the isocyante (II), in such a way that it does not interfere with the decomposition reaction of the urethane (I). These high boiling organic solvents can be chosen from aromatic hydrocarbons, such as alkylbenzenes containing from 9 to 14 carbon atoms in the linear or branched alkyl chain, methylnaphthalene, phenylnaphthalene, benzyl naphthalene and diphenyl; aliphatic hydrocarbons such as linear alkanes containing from 12 to 18 carbon atoms in the molecule; and ethers such as diphenyl ether, methylphenyl ether, cetylphenyl ether and p-nonylphenyl cetyl ether.

It is convenient in stage (a) to operate at boiling conditions, at a temperature of from 220° to 350° C., at atmospheric pressure or at a reduced or increased pressure, and with a residence time of from 1 to 20 minutes.

In stage (b) it is convenient to operate at a temperature ranging from 150° to 200° C., partially evaporating the isocyanate, and consequently maintaining, in the residual liquid mixture, from 0.1 to 0.2 equivalent isocyanate functions and from 0.05 to 0.3 equivalent urethane functions, for every kg of the mixture. The above residual liquid mixture is recycled at stage (a), preferably with previous partial blowdown, in order to keep the content of impurities in the system at a constant or almost constant level. When this kind of blowdown is carried out, it is necessary to also feed a reintegrating flow of the solvent in stage (a).

In stage (c) the distillation is carried out at a pressure which is sufficient to obtain the condensation of the flow of isocyanate vapors, at the head of the column, at a temperature ranging from 80° to 150° C. In the preferred method, the liquid removed from the bottom of the distillation column in stage (c) is recycled in stage (a).

The drawing herein is an illustration of the equipment used in the invention process.

The preferred method of the process of the present invention is now described, with reference being made to FIG. 1. In particular, in this Figure, stage (a) of the process is carried out in reactor R-1, which is kept at a temperature of from 220° to 350° C., at boiling conditions of the reaction mixture, over a period ranging from 1 to 20 minutes. A sufficient supply of heat is given to produce an hourly quantity by weight of vapors of from 1.5 to 2 times the quantity by weight of liquid present in the reactor. These vapors are continuously condensed in EC-1 at a suitable temperature. A flow (6) composed of pure urethane and possibly a reintegrating flow (7) of solvent corresponding to the quantity discharged in (5) are continuously fed into R-1 which, at steady condition, for every kg of liquid contains from 0.3 to 0.5 equivalent isocyanate functions and from 0.2 to 0.5 equivalent urethane functions. In addition, a recycling flow (4) from stage (b) which, for every kg of liquid, contains from 0.1 to 0.2 equivalent isocyanate functions and from 0.05 to 0.3 equivalent urethane functions in the reaction solvent, together with a flow (9) coming from stage (c) which, for every kg of liquid, contains from 0.02 to 0.9 equivalent isocyanate functions and from 0.05 to 1.0 equivalent urethane functions in the reaction solvent, is fed into reactor R-1.

A flow of vapors (1) is continuously withdrawn from reactor R-1, and fractionated in EC-1, this flow being basically composed of alcohol, reaction co-product and a reaction liquid flow (2) which, as specified above, for every kg of liquid, contains from 0.2 to 0.5 equivalent isocyanate functions and from 0.1 to 0.3 equivalent urethane functions in the reaction solvent.

Stage (b) of the process is carried out in a flash chamber C-1, kept under non-reaction conditions, at a temperature ranging from 150° to 200° C. and at a reduced pressure. In particular, a liquid flow (2) having the above composition, is continuously fed to C-1, after being cooled in E-1, at a temperature ranging from 150° to 200° C. A flow of vapors (3) is withdrawn from C-1 in a weight ratio with (2) of from 0.025/1 to 0.2/1. This flow is condensed, either completely or partially, in EC-3 and contains, for every kg of liquid, from 0.1 to 0.2 equivalent isocyanate functions and from 0.05 to 0.3 equivalent urethane functions in the solvent. In addition, a liquid flow (4) having the above composition, is withdrawn and recycled by means of pump P-1 in stage (a), after blowdown in (5). In the preferred method, the isocyanate, urethane and solvent will be recovered from this blowdown.

Stage (c) of the process is carried out in the distillation column C-2, operating at a sufficient head pressure as to allow the condensation of the isocyanate within a temperature range of from 80° to 150° C. A liquid flow (3) having the above composition is continuously fed into C-2. A flow of vapors (8) is withdrawn from C-2, and is condensed in EC-4, in a weight ratio with (3) of from 0.1/1 to 0.5/1. This flow (8) is basically composed of pure isocyanate having the same molar content as that fed into (6). A liquid flow (9), having the above composition, is also withdrawn from C-2. This flow (9), as previously mentioned, is recycled to the first stage.

The procedure of the present invention allows highly selective isocyanate to be produced, even without the use of a catalyst. In fact, the procedure herein described combines the advantages of a low conversion reaction by the flow of urethane and the continual removal of the isocyanate from the system, producing an almost complete selectivity in the reaction main products. In addition, the separate removal of the two products of the decomposition reaction from the system carried out in two distinct phases but integrated with each other gives a better yield of the product.

EXAMPLE 1

In the present example, and in the examples which follow, the equipment illustrated in FIG. 1 is used, where: R-1 is a reactor kept under stirring for the thermal decomposition of the urethane (stage (a)); C-1 is an adiabatic flash chamber (stage (b)); C-2 is a continuous distillation column (stage (c)); EC-1, EC-2, EC-3 and EC-4 are condensers; E-1 is an on-line heat exchanger; V-1 is the tank, with possible heating, of the urethane to be fed; V2, V4 and V5 are containers to collect the condensates in the three respective stages of the process; V3 is a recycling receiver from stage (b) to stage (a) volumetrically operated by pump P-1. In particular, V3, V4 and V5 are equipped with a vacuum outlet. FV-1 and FV-2 are regulation valves for the flow of liquids from stage (a) to stage (b) and from stage (c) to stage (a) respectively. Condensers EC-1, EC-2, EC-3 and EC-4 are initially brought to the respective temperatures of 80°, −10°, 20° and 20° C. E-1 is brought to a temperature which is higher than the flash temperature but which is sufficient to block the reaction, normally to 200° C.

R-1 at steady condition contains 1.24 kg of liquid having the following composition: 93% by weight of inert solvent composed of a mixture of $C_9$-$C_{14}$-alkylbenzenes (in average $C_{10}$-alkylbenzene, hereafter referred to as DDB), 2.2–3.4% by weight of cyclohexyl isocyanate (CHI), 3.1–1.5% by weight of methyl N-cyclohexyl urethane (CHU) and 2.2% by weight of other products.

R-1 operates at the boiling condition of the liquid at 265° C. with a supply of heat as to obtain a flow of condensed vapors from EC-1 equal to 4.3 kg/hour. Moreover, the average operating residence time of R-1 is 12.0 minutes (calculated as the ratio between the volumetric feeding capacity and the weight of the stationary liquid in the reactor). C-1 operates under adiabatic conditions by feeding a liquid kept at 200° C. into E-1, with a contact time of about 2 seconds. Moreover C-1 operates at a pressure which is sufficient to obtain a flow of condensed vapors into EC-3 in a weight ratio with the feeding equal to 0.03/1; said pressure is normally 100 mm Hg. C-2 operates at a pressure, measured at the head, which is sufficient to cause the condensation of CHI at 85° C., normally at 50 mm Hg and with a supply of heat as to obtain a flow of condensed vapors in EC-4 in a weight ratio with the feeding at C2 equal to 0.5/1, with a reflux ratio of 1.5/1.

Under these conditions, a flow (6) of 0.1 kg/hour of 99.6% by weight of CHU (liquid at 75° C.) is fed into R-1, which under the conditions applied to the system undergoes complete conversion. In addition, a flow (7) of 0.038 kg/hour of fresh DDB is continuously fed into R-1. A recycled flow (4), having a composition of: 2.3% by weight of CHI, 1.36% by weight of CHU, 2.27% by weight of other products and 94.0% by weight of DDB, (after a discharge of 0.04 kg/hour in (5)), is fed back into reactor R-1 at a flow rate of 5.99 kg/hour. Finally, a flow (9) is fed to reactor R-1, from stage (c), in quantities of 0.09 kg/hour and having the following composition: 0.44% by weight of CHI, 12.6% by weight of CHU and 87% by weight of DDB.

A flow of vapors (1) (fractionated in EC-1), of which 99.4% by weight is composed of methanol and the remaining percentage of CHU, is withdrawn continuously from reactor R-1 in quantities of 0.019 kg/hour. A liquid reaction flow (2) having the following composition: 3.4% by weight of CHI, 1.5% by weight of CHU, 2.2% by weight of other products and 98.2% by weight of DDB is also continuously withdrawn from reactor R-1 with a flow rate of 6.2 kg/hour.

Flow (2) is continuously fed to C1 from which a liquid flow (4) having the above composition and with a flow rate of 6.04 kg/hour, is withdrawn. A flow of vapors (3) is also withdrawn and condensed, with an hourly flow rate of 0.16 kg and the following composition: 45.1% by weight of CHI, 6.98% by weight of CHU and 47.8% by weight of DDB.

This latter flow (3) is continuously fed to C2, from which a liquid flow (9) having the above composition is withdrawn together with a flow of vapors (8) which are condensed and withdrawn with a flow rate of 0.0739 kg/hour, comprising the main reaction product with a 99% by weight purity.

From the above data it can be calculated that, under steady conditions:
the conversion of CHU, per run, is equal to 51.4%
the selectivity with respect to CHI is equal to 94.6%,
the productivity is equal to 59.6 g of CHI per liter of reactor, per hour.

EXAMPLE 2

The same procedure is used as for Example 1, with the equipment of FIG. 1. In particular, a flow (6) of FMU (methyl N-phenylurethane) is fed to R-1 at 0.114 kg/hour, which under the conditions imposed, is completely converted. In addition, a flow of fresh DDB (7) is fed into R-1 at 0.0479 kg/hour. A recycled flow (4) having the following composition: 1.85% by weight of FI (phenyl isocyanate), 4.21% by weight of FMU, 2.88% by weight of other products and 91% by weight of DDB and with a flow rate of 5.91 kg/hour is also fed to R-1, from stage (b) (after a discharge of 0.05 kg/hour in (5)). Finally, a flow (9) having following composition: 1.76% by weight of FI, 10.5% by weight of FMU and 87.3% by weight of DDB is fed to reactor R-1, from stage (c), in quantities of 0.085 kg/hour.

A flow of vapors (1) (fractionated in EC-1), of which 99.5% is methanol and the remaining percentage FMU, is continuously withdrawn from reactor R-1 in quantities of 0.0236 kg/hour. A liquid reaction flow (2) having the following composition: 3.2% by weight of FI, 4.24% by weight of FMU, 2.81% by weight of other products and 89.7% by weight of DDB, and with a flow rate of 6.13 kg/hour, is continuously withdrawn from reactor R-1.

Flow (2) is continuously fed to C-1, from which a liquid flow (4) having the above composition and with a flow rate of 5.96 kg/hour, is withdrawn. A flow of vapors (3) having the following composition: 50.6% by weight of FI, 5.3% by weight of FMU and 43.6% by weight of DDB and with a flow rate of 0.17 kg/hour is also withdrawn and condensed.

This latter flow is continuously fed to C-2, from which a liquid flow (9) having the above composition is withdrawn together with a flow of vapors (8) which are condensed and withdrawn with a flow rate of 0.0845 kg/hour, comprising the main reaction product with a 99% purity by weight.

From the above data, it can be calculated that, under steady conditions:
the conversion of FMU, per run, is equal to 30.1%,
the selectivity with respect to FI is equal to 96.7%, and
the productivity is equal to 68.14 g of FI per liter of reactor, per hour.

EXAMPLE 3

The same equipment is used as in FIG. 1, under the same conditions as those described in Example 1, but keeping a temperature of 280° C. and a residual pressure of 190 mm Hg in R-1. In particular, a flow (6) of 0.156 kg/hour of NDU (1,6-dimethyl hexamethylenediurethane) is fed to R-1 and, under the conditions imposed, is completely converted. In addition, a recycled flow (4) is fed into R-1 from stage (b) with a flow rate of 5.07 kg/hour and with the following composition: 0.53% by weight of HDI (1,6-hexamethylene diisocyanate), 2.09% by weight of HMI (monoisocyanate hexamethylene monourethane), 1.01% by weight of HDU and 96.4% by weight of solvent (diphenyl alkylate). Finally, a flow (9) is fed to reactor R-1, from stage (c), in quantities of 0.961 kg/hour, and having the following composition: 11.45% by weight of HMI, 0.36% by weight of HDU and 88.2% by weight of solvent.

A flow of vapors (1) (fractionated in EC-1) is continuously withdrawn from reactor R-1 in quantities of 0.043 kg/hour, of which 99.5% consists of methanol, the remaining percentage being HDU and slight fractions of solvent. A liquid reaction flow (2) is continuously removed from reactor R-1, with a flow rate of 6.14 kg/hour and with the following composition: 2.27% by weight of HDI, 3.51% by weight of HMI, 0.89% by weight of HDU and 93.3% by weight of solvent.

Flow (2) is continuously fed to C-1, from which a liquid flow (4) having the above composition is removed with a flow rate of 5.07 kg/hour. A flow of vapors (3) is also removed, which are condensed with a flow rate of 1.075 kg/hour and having the following composition: 10.5% by weight of HDI, 10.2% by weight of HMI, 0.32% by weight of HDU and 78.9% by weight of solvent.

The latter flow is continuously fed to C-2, from which a liquid flow (9), having the above composition, is withdrawn together with a flow of vapors (8) which are condensed and withdrawn with a flow rate of 0.113 kg/hour, comprising the main reaction product with a 99% purity by weight.

From the above data, it can be calculated that, under steady conditions:
the conversion of HDU, per run, is equal to 74%,
the selectivity with respect to HMI is equal to 71.6%
the selectivity with respect to HDI is equal to 28.4% and
the productivity is equal to 91 g of HDI per liter of reactor, per hour.

We claim:

1. A continuous process for the production of an organic mono- or di-isocyanate from the corresponding urethane, according to the following reaction:

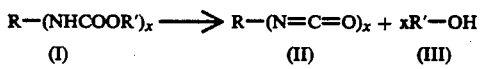

$$R-(NHCOOR')_x \longrightarrow R-(N=C=O)_x + xR'-OH$$
$$(I) \qquad\qquad (II) \qquad\quad (III)$$

where
R represents a C3–C18 alkyl radical, with a linear or branched chain, optionally having one or more ethylenic unsaturations; a C5–C7 cycloalkyl radical; or a monocyclic or polycyclic aryl radical, with condensed or uncondensed rings; said radicals optionally having one or more substituents chosen from the group consisting of C1–C4 alkyl, C1–C4 alkoxy, nitro, chloro, fluoro and bromo groups;
R' represents a C1–C20 alkyl group; and
x is 1 or 2;
said process being characterized by the fact that:
(a) a flow of urethane (I) is continuously fed to a decomposition reactor containing a liquid mixture, having a substantially constant volume and composition and without any catalytic substances for the decomposition reaction, composed of a high boiling, inert, organic solvent containing unaltered urethane (I) in a concentration of from 0.05 to 1.0 equivalent urethane functions and isocyanate (II) in a concentration of from 0.02 to 0.9 equivalent isocyanate functions for every kg of the liquid mixture, the above reactor being kept at the boiling temperature of the solvent and at the decomposition temperature of the urethane (I) in isocyanate (II) and alcohol (III), the decomposition rate of the urethane (I) corresponding to the rate at which it is fed to the reactor, the alcohol (III) being evaporated at a rate which corresponds more or less to that of its formation;
(b) the liquid mixture is continuously withdrawn from the reactor in (a) at a rate which does not substantially alter the volume of the mixture in (a) and is fed to a flash apparatus kept at a temperature which is lower than the decomposition temperature of the urethane (I), in said apparatus, the isocyanate (II) being partially evaporated at a rate which corresponds to that of its formation in the reactor in (a), the residual liquid mixture of the flash being recycled to the reactor in (a); and
(c) the flow of vapor generated in (b) is continuously withdrawn, condensed and distilled, in a distillation column, to separate the isocyanate (II), which is the product at the head of the column, in a pure or substantially pure form.

2. The process according to claim 1, characterized by the fact that R in the formulae represents an aryl radical deriving from an aromatic monoamine, or ortho-, meta-, or para-substituted anilines with an alkyl group or with a group containing a halogen; an alkyl radical deriving from an aliphatic monoamine; an alkyl radical deriving from an aliphatic diamine; and R' represents a methyl group.

3. The process according to claim 1, characterized by the fact that the urethane (I) is chosen from the group consisting of methyl N-phenyl urethane, methyl N-p-methoxyphenyl urethane, methyl N-p-chlorophenyl urethane, methyl N-m-(trifluoromethyl) phenyl urethane, methyl N-cyclohexyl urethane, methyl N-butyl urethane, 3-methoxycarbonyl amino-3,5,5-trimethyl methoxycarbonylamino cyclohexyl urethane, and 1,6-dimethyl hexamethylene urethane.

4. The process according to claim 1, characterized by the fact that the solvent, used in stage (a), is an organic solvent with a boiling point of at least 40°–50° C. higher than that of the isocyanate (II), chosen from the group consisting of aromatic hydrocarbons, aliphatic hydrocarbons and ethers.

5. The process according to claim 1, characterized by the fact that in stage (a) the operating temperature ranges from 220° to 350° C. over a period of from 1 to 20 minutes.

6. The process according to claim 1, characterized by the fact that in stage (b) the operating temperature ranges from 150° to 200° C. partially evaporating the isocyanate, and constantly maintaining, in the residual liquid mixture, from 0.1 to 0.2 equivalent isocyanate functions and from 0.05 to 0.3 equivalent urethane functions, for every kg of the mixture.

7. The process according to claim 1, characterized by the fact that the liquid mixture recycled from stage (b) to stage (a) is submitted to partial blowdown, to keep the content of impurities in the system at a constant or almost constant level, and a flow of reintegrating solvent equal to that which has been discharged is also fed to stage (a).

8. The process according to claim 1, characterized by the fact that in stage (c) the distillation is carried out at a pressure which is sufficient to cause the condensation of the flow of isocyanate vapors, at the head of the column, at a temperature of from 80° to 150° C. and the residual liquid mixture of the distillation is recycled to stage (a).

* * * * *